United States Patent [19]

Iwasaki et al.

[11] Patent Number: 4,786,634
[45] Date of Patent: Nov. 22, 1988

[54] METHOD FOR TREATING ARTERIOSCLEROSIS

[75] Inventors: Hitoshi Iwasaki, Tokyo; Kazuyuki Kitamura, Urawa; Akio Ohtani, Warabi, all of Japan

[73] Assignee: Tanabe Seikyaku Co., Ltd., Osaka, Japan

[21] Appl. No.: 49,169

[22] Filed: May 12, 1987

[30] Foreign Application Priority Data

May 23, 1986 [JP] Japan .................. 61-119928

[51] Int. Cl.$^4$ .............................................. A61K 31/55
[52] U.S. Cl. .................................... 514/211; 514/824
[58] Field of Search ................ 514/211, 824; 540/491

[56] References Cited

U.S. PATENT DOCUMENTS 4,567,175  1/1986  Takeda et al. ..................... 514/211

FOREIGN PATENT DOCUMENTS 0127882  12/1984  European Pat. Off.

OTHER PUBLICATIONS

Sugano et al., "Suppression of Atheroschlerosis in Cholesterol Fed Rabbits by Diltiazem Injection," Arterioschlerosis 6:237–241, Mar./Apr. 1986.

Primary Examiner—Jerome D. Goldberg
Assistant Examiner—R. M. Kearse
Attorney, Agent, or Firm—Scully, Scott, Murphy & Presser

[57] ABSTRACT

There are disclosed a prophylactic and curing composition for arteriosclerosis, comprising as an active ingredient an 8-chloro-1,5-benzothiazepine derivative represented by the formula:

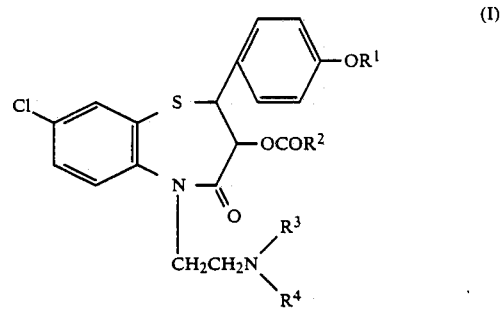

wherein $R^1$, $R^2$, $R^3$ and $R^4$ each represent lower alkyl groups, or a pharmaceutically acceptable salt thereof, and a method of treatment of arteriosclerosis.

8 Claims, No Drawings

METHOD FOR TREATING ARTERIOSCLEROSIS

BACKGROUND OF THE INVENTION

The present invention relates to a novel prophylactic and curing composition for arteriosclerosis, a use of an 8-chlorobenzothiazepine compound for preparing said composition and a method of the prophylaxis or treatment of arteriosclerosis. 2-(4-Methoxyphenyl)-3-alkanoyloxy-5-[2-(dialkylamino)ethyl]-8-chloro-2,3-dihydro-1,5-benzothiazepin-4(5H)-one is a known compound, and it has been known to have excellent hypotensive activity and/or cerebral and coronary vasodilating activity (Japanese Unexamined Patent Publication No. 225174/1984).

However, in the prior art, it has never been known that this compound shows anti-arteriosclerosis activity.

Arteriosclerosis is pathologically classified into the three groups of atherosclerosis, Mönkeberg's sclerosis (medial sclerosis) and arteriolosclerosis. Atherosclerosis is characterized by lipid deposition and plaque formation in the intima of e.g., coronary artery, basilar artery, renal artery, thoracic aorta or abdominal aorta. Mönkeberg's sclerosis is frequently observed in medium-sized arteries in extremities, such as e.g., femoral artery, and characterized by calcification of arterial media. Arteriolosclerosis is a sclerotic change which is observed in arterioles in e.g. the kidney, adrenal gland, spleen, ovary or pancreas.

In recent years, advanced studies have been made about these arteriosclerosis, and it has been considered that non-limited growth of medial smooth muscle cells in the intima of blood vessels and abnormal accumulation of cholesterol within cells can be the causes for such arteriosclerosis, and the relationship between such causes and prostacyclin ($PGI_2$) is now of interest. For example, when a rabbit is fed with a cholesterol-rich diet, it has been known that prostacyclin producing ability of artery is lowered together with the progress of arteriosclerosis of said rabbit.

It is also known that prostacyclin producing ability is lowered at the arteriosclerotic lesion site to a level half or lower of that at normal site [Gendai Iryo (Modern Medical Treatment), 12, 909(1980)].

On the other hand, Hajjar et al report that addition of prostacyclin to a culture system of medial smooth muscle cells from rabbit aorta increases ACEH (Acid cholesteryl ester hydrolase) activity of the cells, whereby deposition of cholesterol within the cells is inhibited [Journal of Clinical Investigation, 70, 479 (1982)]. Further, it is also reported for medial smooth muscle cells from arteriosclerotic lesions that addition of prostacyclin in a culture system lowers the cholesterol content in said cells [Lancet, 2, 521 (1983)].

SUMMARY OF THE INVENTION

The present invention, in view of the state of the art as described above, is intended to provide a novel prophylactic and curing agent for arteriosclerosis having the activity of potentiating prostacyclin producing ability of medial smooth muscle cells of blood vessel and also having anti-arteriosclerosis activity.

The present invention is a prophylactic and curing composition for arteriosclerosis, comprising as an active ingredient an 8-chloro-1,5-benzothiazepine derivative represented by the formula:

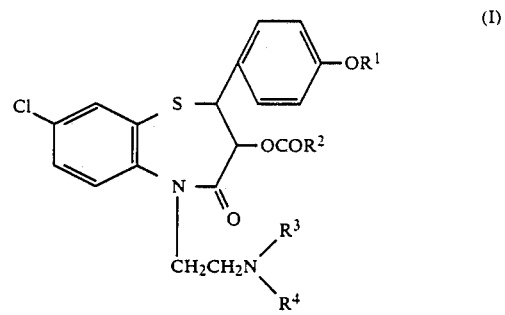

wherein $R^1$, $R^2$, $R^3$ and $R^4$ each represent lower alkyl groups, or an acid addition salt thereof.

The present invention also concerns a use of the compound represented by the formula (I) or a pharmaceutically acceptable salt thereof for preparing said composition.

Still further, the present invention provides a method of the prophylaxis or treatment of arteriosclerosis.

DESCRIPTION OF THE PREFERRED EMBODIMENTS

As the compound (I) which is the active ingredient of the present invention, there may be included compounds wherein $R^1$, $R^2$, $R^3$ and $R^4$ in the above formula are lower alkyl groups such as a methyl group, an ethyl group, a propyl group, a butyl group, a pentyl group or a hexyl group.

Since these compounds have two asymmetric carbons in the molecule, there exist two kinds of stereoisomers (namely cis- and trans-isomers) or 4 kinds of optical isomers (namely, (+)-cis, (−)-cis, (+)-trans and (−)-trans-isomers), and the present invention is inclusive of all of these respective isomers and their mixtures.

However, generally speaking, cis-isomers are preferred as pharmaceuticals.

The compound (I) which is the active ingredient of the present invention potentiates markedly the prostacyclin producing ability of medial smooth muscle cells of blood vessels and also has excellent anti-arteriosclerosis activity.

For example, when (+)-cis-2-(4-methoxyphenyl)-3-acetoxy-5-[2-(dimethylamino)ethyl]-8-chloro-2,3-dihydro-1,5-benzothiazepin-4(5H)-one was added to cultured rat aortic smooth muscle cells for examination of prostacyclin producing ability of said cells, the above compound exhibited excellent activity for potentiating prostacyclin producing ability. Also, when the effect of (+)-cis-2-(4-(4-methoxyphenyl)-3-acetoxy-5-[2-(dimethylamino)ethyl]-8-chloro-2,3-dihydro-1,5-benzothiazepin-4(5H)-one for experimental atherosclerosis in rabbits and Mönkeberg's sclerosis in rats were examined, the above compound exhibited excellent ameliorating effect on either type of arteriosclerosis. Thus, the medicament of the present invention can be used for prophylaxis or treatment of various arteriosclerosis such as atherosclerosis, Mönkeberg's sclerosis (medical sclerosis) and arteriolosclerosis.

The above compound (I) which is the active ingredient in the medicament of the present invention can be used for pharmaceutical uses in the form of either a free base or a pharmaceutically acceptable acid addition salt thereof. Examples of such pharmaceutically acceptable acid addition salts may include inorganic acid addition salts such as hydrochloride, hydrobromide, hydroiodide, perchlorate, sulfate and phosphate or organic acid addition salts such as oxalate, maleate, fumarate, succinate, methanesulfonate or 2-(4-hydroxybenzoyl) benzoate.

The compound (I) or a pharmaceutically acceptable acid addition salt thereof can be administered both orally and parenterally together with excipients suitable for oral or parenteral administration. The medicament of the present invention can be formed into a suitable preparation by use of pharmaceutical carriers conventionally used in either oral or parenteral administration. Such pharmaceutical carriers may include, for example, binding agents (syrup, gum arabic, gelatin, sorbitol, tragacanth gum, polyvinylpyrrolidone, etc.), excipients (lactose, sucrose, corn starch, potassium phosphate, sorbitol, glycine, etc.), lubricants (magnesium stearate, talc, polyethylene glycol, silica, etc.), disintegrators (potato starch, etc.) and wetting agents (sodium laurylsulfate, etc.). Preparation forms may be, e.g., tablets, pills, powders, capsules or granules. Further, for parenteral administration, the medicament may be used in the form of an injection or instillation by use of distilled water for injection, physiological saline, aqueous glucose solution, etc., and also in the form a suspension, dispersion or emulsion which is prepared with the use of glycerine, propylene glycol, simple syrup, ethanol, fatty oils, ethylene glycol or sorbitol.

The dose of the compound (I) or its acid addition salt which is the active ingredient of the present invention may vary according to the age and body weight of the patient and the kind and severity of the disease, but is generally about 0.05 to 60 mg/kg/day, preferably about 0.05 to 10 mg/kg/day, particularly preferably 0.5 to 10 mg/kg/day in the case of oral administration and about 0.05 to 2 mg/kg/day in the case of parenteral administration.

The compound (I) which is the active ingredient of the present invention can be prepared according to, for example, the method disclosed in Japanese Unexamined Patent Publication No. 225174/1984 (which corresponds to U.S. Pat. No. 4,567,175).

Throughout the specification and claims, the term "lower alkyl" should be interpreted as referring to alkyl of one to 6 carbon atoms.

EXAMPLES

The present invention is described in more detail by referring to the following Experimental examples and Examples.

EXPERIMENTAL EXAMPLE 1

(Prostacyclin production promoting activity for aortic smooth muscle cells)

After rat aortic smooth muscle cells (hereinafter called SMC) were grown to confluence in culture dish by using growth medium, the growth medium was removed and preincuvation was conducted with addition of a medium for assay at 37° C. for 15 minutes. Then, the medium was removed and a medium for assay containing a test compound was freshly added, followed by cultivation at 37° C. in 5% $CO_2$-95% air for 24 hours.

After completion of the cultivation, the prostacyclin production promoting activity of the test compound was examined by assaying the stable prostacyclin metabolite (6-KetoPGF$_1\alpha$) existing in the supernatant according to radioimmunoassay. As the test compound, (+)-cis-2-(4-methoxyphenyl)-3-acetoxy-5-[2-(dimethylamino)ethyl]-8-chloro-2,3-dihydro-1,5-benzothiazepin-4(5H)-one maleate was employed.

(Note) The respective media used in the above experiment had the following compositions.

Growth medium for proliferation: Eagle's Minimum Essential Medium + 10% fetal calf serum Medium for assay: Eagle's Minimum Essential Medium + 10 mM N-2-hydroxyethylpiperazine-N-2-ethanesulfinic acid (pH 7.4)

<Results>

The results are shown in the following Table 1. It was recognized that the prostacyclin producing ability was increased to about 1.8-fold in the case of adding the test compound as compared with the case of no addition.

TABLE 1

| Concentration of test compound added | Amount of 6-KetoPGF$_1\alpha$ produced (pg/24 h/1 × 10$^6$ cells) |
|---|---|
| No addition | 129 ± 20 |
| 1 × 10$^{-5}$ M | 226 ± 32 |

EXPERIMENTAL EXAMPLE 2

(Effect on atherosclerosis)

Rabbits (male, weight: about 2.4 Kg, one group: 10 rabbits) were fed with a lipid-rich diet (prepared by adding cholesterol (0.5%) and soybean oil (3%) to normal diet) for 12 weeks.

On the other hand, in order to examine the effect of the test compound on the arteriosclerosis in the aorta induced under such experimental conditions, an aqueous solution of the test compound (30 mg/kg) was administered to the animals with a stomach tube once a day at a fixed time simultaneously with initiation of dieting with the lipid-rich diet. Twelve weeks after initiation of the experiment, rabbits were killed under anesthesia (ether and pentobarbital were used in combination), and the proportion of the atheroma in the intima of the arotic arch and thoracic aorta (atheroma formation ratio) was examined.

As the test compound, (+)-cis-2-(4-methoxyphenyl)-3-acetoxy-5-[2-(dimethylamino)ethyl]-8-chloro-2,3-dihydro-1,5-benzothiazepin-4(5H)-one maleate was used. <Results>

The results are shown in Table 2, and it can be clearly seen that in the group administered the test compound atheroma formation ratio is lower as compared with that in the non-administration group.

This effect in the group administered the test compound suggests that the atheromatous changes, namely deposition of cholesterol in the blood vessel wall, atheroma formation accompanied with an increase in connective tissue filters in the intima and subsequent ulcer formation by breaks of said atheroma, are inhibited by the prostacyclin production potentiating effect of the compound of the present invention.

TABLE 2

|  | Atheroma formation rate (%) |
|---|---|
| Test compound non-administration group | 51.2 ± 5.6 |
| Test compound administration group | 38.4 ± 5.8 |

EXPERIMENTAL EXAMPLE 3

(Effect on Mönkeberg's sclerosis)

Spontaneously hypertensive rats (male, age: 12 weeks, one group: 14-15 rats) were fed with a lipid-rich diet (prepared by adding cholesterol (3%), hydrogenated cotton seed oil (7%), cholic acid (0.5%) and thiouracil (0.3%) to normal diet) for 7 days, and further, for first four days, vitamin $D_2$ (8 mg/kg) was administered to the animals with a stomach tube in the form of a solution in olive oil (2 ml/kg) once at a fixed time every day. In order to examine the effect of the test compound on Mönkeberg's sclerosis of the aorta induced under such experimental conditions, an aqueous solution of the test compound was administered to the animals with a stomach tube one hour and 7 hours after the administration of vitamin $D_2$ for 4 days, and further administration of the test compound alone was continued twice per day for the next 3 days.

On the 7th day after initiation of the experiment, the rats were killed under ether anesthesia and the lesions were examined.

As the test compound (+)-cis-2-(4-methoxyphenyl)-3-acetoxy-5-[2-(dimethylamino)ethyl]-8-chloro-2,3-dihydro-1,5-benzothiazepin-4(5H)-one maleate was used.

<Results>

The results are shown in Table 3, and it can be clearly seen that the incidence of lesions is lowered in the group treated with the test compound.

TABLE 3

| Lesions | Dose of test Compound | |
|---|---|---|
| | 0 | 30 mg × 2/kg/day |
| Subdural hemorrhage | 11/14 | 8/15 |
| Periaortic hemorrhage | 7/14 | 3/15 |
| Subcutaneous hemorrhage | 7/14 | 3/15 |

(In the numerical values in the Table, denominator indicates the number of rats used in the experiment, and numerator the number of rats in which lesions were recognized.)

EXAMPLE 1

| (Tablet) | |
|---|---|
| (+)-Cis-2-(4-methoxyphenyl)-3-acetoxy-5-[2-(dimethylamino)ethyl]-8-chloro-2,3-dihydro-1,5-benzothiazepin-4(5H)—one maleate | 45.0 g |
| Corn starch | 20.1 g |
| Lactose | 82.4 g |
| Polyvinylpyrrolidone | 3.0 g |
| Crystalline cellulose | 38.0 g |
| Magnesium stearate | 1.5 g |
| Total | 190.0 g |

The medicament, lactose and corn starch were mixed with an alcohol solution of polyvinylpyrrolidone and granulated by kneading according to the wet granulation method, followed by drying to be formed into granules.

Subsequently, magnesium stearate and crystalline cellulose were added to the granules and the mixture is compressed to obtain tablets of 8 mm in diameter and 190 mg in weight.

EXAMPLE 2

(Injection)

(+)-Cis-2-(4-methoxyphenyl)-3-acetoxy-5-[2-(dimethylamino)ethyl]-8-chloro-2,3-dihydro-1,5-benzothiazepin-4(5H)-one maleate (10 g) was dissolved in 2 liter of distilled water for injection. The solution was filtered through a membrane filter with a pore size of 0.22 μm, and is poured into ampoules under sterilization conditions each in 2 ml and sealed to give ampoules for injection.

We claim:

1. A method for the treatment of arteriosclerosis in a warm-blooded animal in need thereof comprising administering to said animal an anti-arteriosclerotic effective amount of an 8-chloro-1,5-benzothiazepine derivative represented by the formula:

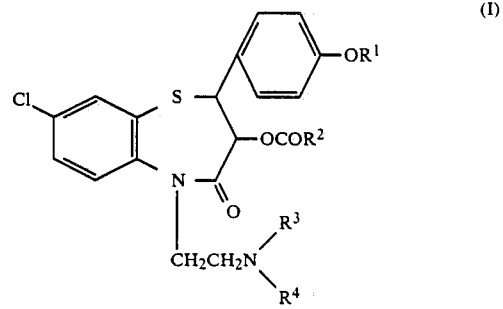

wherein $R^1$, $R^2$, $R^3$ and $R^4$ each represent lower alkyl groups, or a pharmaceutically acceptable salt thereof.

2. The method according to claim 1, wherein the compound to be administered is (+)-cis-2-(4-methoxyphenyl)-3-acetoxy-5-[2-(dimethylamino)ethyl]-8-chloro-2,3-dihydro-1,5-benzothiazepin-4(5H)-one or a pharmaceutically acceptable salt thereof.

3. The method according to claim 1, wherein the dose of the compound represented by the formula (I) or its pharmaceutically acceptable salt is about 0.05 to 10 mg/kg/day.

4. The method according to claim 3, wherein the dose is about 0.5 to 10 mg/kg/day.

5. The method according to claim 1, for the treatment of atherosclerosis, Mönkeberg's sclerosis or arteriolosclerosis.

6. The method according to claim 1, for the treatment of atherosclerosis.

7. The method according to claim 1, for the treatment of Mönkeberg's sclerosis.

8. The method according to claim 1, for the treatment of arteriolosclerosis.

* * * * *